(12) United States Patent
Barlaam et al.

(10) Patent No.: US 7,226,945 B2
(45) Date of Patent: Jun. 5, 2007

(54) ESTROGEN RECEPTOR-β LIGANDS

(75) Inventors: Bernard Barlaam, Reims (FR); James J. Folmer, Wilmington, DE (US); Timothy M. Piser, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 330 days.

(21) Appl. No.: 10/399,010

(22) PCT Filed: Oct. 10, 2001

(86) PCT No.: PCT/SE01/02223

§ 371 (c)(1),
(2), (4) Date: Apr. 10, 2003

(87) PCT Pub. No.: WO02/30407

PCT Pub. Date: Apr. 18, 2002

(65) Prior Publication Data

US 2004/0039015 A1 Feb. 26, 2004
US 2005/0043350 A9 Feb. 24, 2005

Related U.S. Application Data

(60) Provisional application No. 60/239,964, filed on Oct. 13, 2000, provisional application No. 60/240,251, filed on Oct. 13, 2000.

(51) Int. Cl.
*A61K 31/35* (2006.01)
(52) U.S. Cl. ............... 514/456; 514/457; 549/289
(58) Field of Classification Search ........ 549/289, 549/362; 514/456, 457
See application file for complete search history.

(56) References Cited

U.S. PATENT DOCUMENTS

| 5,733,926 | A | 3/1998 | Gobach | |
| 6,331,562 | B1 * | 12/2001 | Bhagwat et al. | 514/457 |
| 6,518,301 | B1 * | 2/2003 | Barlaam et al. | 514/444 |

FOREIGN PATENT DOCUMENTS

| EP | 0135172 | 3/1985 |
| WO | WO 9844920 | 10/1998 |
| WO | WO 9850026 | 11/1998 |
| WO | WO 00/62765 | * 10/2000 |
| WO | WO 0062765 | 10/2000 |

OTHER PUBLICATIONS

Kitagawa, M et al, 'Aryloxyacetic acid diuretics with uriosuric activity. II. Substituted [(4-oxo-4H-1-benzopyran-7-yl)oxy]acetic acids and the related compounds' CA 116:106034 (1992).*
Barlaam, B et al, 'Estrogen receptor-Beta ligands for therapy' CA 133:317571 (2000).*
Anthony, M. et al 'What would be the properties of an ideal serm?' Annals of the New York Academy of Sciences, (Dec. 2001) 949, 261-278.*
Zhao Bian et al, "Selective Estrogen Receptor Modulators and Coronary Heart Disease," Trends in Cardiovascular Medicine, vol. 11 (No. 2), p. 196-202, fig. 1.
Valerie L. Baker et al, "Selective Estrogen Receptor Modulators in Reporductive Medicine and Biology," Obstetical and Gynecological Survey, vol. 55 (No. 7), p. 21-47, fig. 1.
Y.T. Van Der Schouw et al, "Phytoestrogens and cardiovascular disease risk," Nutr. Metab. Cardiovasc. Dis., p. 154-157, fig. 1.
Joe A. Vison et al, "Plant Flavonoids, Especially Tea Flavonols, Are Powerful Antioxidants Using an in Vitro Oxidation Model for Hearth Disease," J. Agric. Food Chem., p. 2800-2802, fig. 1.
J.J.B. Anderson et al, "Biphasic Effects of Genistein on Bone Tissue in the Ovariectomized, Lactating Rat Model," Society of the Society for experimental biology and medicine, p. 345-350, fig. 1.
John JB Anderson et al, "Health potential of soy isoflavones for menopausal women," Public Health Nutration, vol. 2 (No. 4), p. 489-504, fig. 1.
Ann Vincent et al, "Soy Isofavones: Are they useful in menopause?," Mayo Clinic Proc, p. 1174-1184, fig. 1.
J. Huber, "Phytoostrogene und SERMs, Alternativen zur klassischen Hormontherapie?,"Therapeutische Umschau, p. 651-654.

* cited by examiner

*Primary Examiner*—Amelia A. Owens
(74) *Attorney, Agent, or Firm*—White & Case LLP

(57) ABSTRACT

A method for treating a disease associated with the estrogen receptor-β, comprising the step of administiering a therapeutically-effective amount of a compound that satifies the equation: $K_{i\alpha A}/K_{i\beta A}>25$, optionally having general structure (I).

1 Claim, No Drawings

ESTROGEN RECEPTOR-β LIGANDS

This application claims the benefit of U.S. Provisional Application No. 60/239,964, filed Oct. 13, 2000 and U.S. Provisional Application No. 60/240,251, filed Oct. 13, 2000.

TECHNICAL FIELD

The present invention is directed to a series of ligands, and more particularly to estrogen receptor-β ligands which have better selectivity than estrogen for the estrogen receptor-β over the estrogen receptor-α, as well as to methods for their production and use in the treatment of diseases related to the estrogen receptor-β, specifically, Alzheimer's disease, anxiety disorders, depressive disorders, osteoporosis, cardiovascular disease, rheumatoid arthritis, or prostate cancer.

BACKGROUND

Estrogen-replacement therapy ("ERT") reduces the incidence of Alzheimer's disease and improves cognitive function in Alzheimer's disease patients (Nikolov et al. Drugs of Today, 34(11), 927–933 (1998)). ERT also exhibits beneficial effects in osteoporosis and cardiovascular disease, and may have anxiolytic and anti-depressant therapeutic properties. However, ERT shows detrimental uterine and breast side effects that limit its use.

The beneficial effects of ERT in post-menopausal human women is echoed by beneficial effects of estrogen in models relevant to cognitive function, anxiety, depression, bone loss, and cardiovascular damage in ovariectomized rats. Estrogen also produces uterine and breast hypertrophy in animal models reminiscent of its mitogenic effects on these tissues in humans.

The beneficial effects of ERT in post-menopausal human women is echoed by beneficial effects of estrogen in models relevant to cognitive function, anxiety, depression, bone loss, and cardiovascular damage in ovariectomized rats. Specifically, experimental studies have demonstrated that estrogen effects the central nervous system ("CNS") by increasing cholinergic function, increasing neurotrophin/neurotrophin receptor expression, altering amyloid precursor protein processing, providing neuroprotection against a variety of insults, and increasing glutamatergic synaptic transmission, among other effects. The overall CNS profile of estrogen effects in pre-clinical studies is consistent with its clinical utility in improving cognitive function and delaying Alzheimer's disease progression. Estrogen also produces mitogenic effects in uterine and breast tissue indicative of its detrimental side effects on these tissues in humans.

The estrogen receptor ("ER") in humans, rats, and mice exists as two subtypes, ER-α and ER-β, which share about a 50% identity in the ligand-binding domain (Kuiper et al. Endocrinology 139(10) 4252–4263 (1998)). The difference in the identity of the subtypes accounts for the fact that some small compounds have been shown to bind preferentially to one subtype over the other (Kuiper et al.).

In rats, ER-β is strongly expressed in brain, bone and vascular epithelium, but weakly expressed in uterus and breast, relative to ER-α. Furthermore, ER-α knockout (ERKO-α) mice are sterile and exhibit little or no evidence of hormone responsiveness of reproductive tissues. In contrast, ER-β knockout (ERKO-β) mice are fertile, and exhibit normal development and function of breast and uterine tissue. These observations suggest that selectively targeting ER-β over ER-α could confer beneficial effects in several important human diseases, such as Alzheimer's disease, anxiety disorders, depressive disorders, osteoporosis, and cardiovascular disease without the liability of reproductive system side effects. Selective effects on ER-β-expressing tissues (CNS, bone, etc.) over uterus and breast could be achieved by agents that selectively interact with ER-β over ER-α.

It is a purpose of this invention to identify ER-β-selective ligands that are useful in treating diseases in which ERT has therapeutic benefits.

It is another purpose of this invention to identify ER-β-selective ligands that mimic the beneficial effects of ERT on brain, bone and cardiovascular function.

It is another purpose of this invention to identify ER-β-selective ligands that increase cognitive function and delay Alzheimer's disease progression.

SUMMARY OF THE INVENTION

This present invention is directed to the use of ligands having the generic structure:

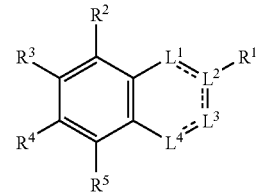

as ER-β-selective ligands, which mimic ERT, but lack undesirable side effects of ERT. These ligands particularly satisfy the formula:

$$K_{i\alpha A}/Ki_{\beta A} > 25,$$

preferably:

$$K_{i\alpha A}/Ki_{\beta A} > 50,$$

more preferably:

$$K_{i\alpha A}/Ki_{\beta A} > 100,$$

wherein $K_{i\alpha A}$ is the $K_i$ value for the ligand in ER-α; $K_{i\beta A}$ is the $K_i$ value for the ligand in ER-β.

DETAILED DESCRIPTION OF THE INVENTION

The instant invention involves a method for the treatment or prophylaxis of a disease associated with the estrogen receptor-β, comprising the step of administering a therapeutically-effective amount of a ligand that satisfies the equation:

$$K_{i\alpha A}/Ki_{\beta A} > 25,$$

wherein $K_{i\alpha A}$ is the $K_i$ value for the ligand in ER-α and $K_{i\beta A}$ is the $K_i$ value for the ligand in ER-β. Preferably, $K_{i\alpha A}/Ki_{\beta A} > 50$ and more preferably $K_{i\alpha A}/Ki_{\beta A} > 100$.

Ligands suitable for the above use have the structure:

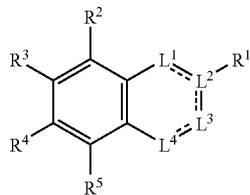

wherein: $L^1$ is —C(=O)—, =C($R^6$)—, —CH($R^6$)—, O, S, or N$R^a$; $L^2$ is =C— or —CH—; $L^3$ is =C($R^6$)—, —CH($R^6$)— or —C(=O)—; $L^4$ is —C(=O)—, CH$_2$, O, S, or N$R^a$; wherein: when $L^1$ is —C(=O)—, $L^4$ is CH$_2$, O, S, or N$R^a$; when $L^4$ is —C(=O)—, $L^1$ is CH$_2$, O, S, or N$R^a$; when $L^3$ is —C(=O)—, $L^1$ is =C($R^6$)— or —CH($R^6$)—, and $L^4$ is O or N$R^a$; when $L^1$ is =C($R^6$)—, $L^2$ is =C—; when $L^1$ is —CH($R^6$)—, $L^2$ is —CH—; when $L^3$ is =C($R^6$)—, $L^2$ is =C—; and when $L^3$ is —CH($R^6$)—, $L^2$ is —CH—; $R^a$ is, independently, at each occurrence, H or (C$_1$–C$_5$)alkyl; $R^1$ is phenyl, substituted phenyl or Het; $R^2$ is selected from —S$R^a$, —N$R^a$$R^a$, —NC(=O)$R^a$, —NS(=O)$R^a$, —NS(=O)$_2$$R^a$, halogen, cyano, haloC$_{1-6}$alkyl, —CO$_2$$R^a$, —C(=O)$R^a$, —C(=O)NH$R^a$, nitro, —S(=O)$R^a$ and —S(=O)$_2$$R^a$; $R^3$, $R^4$ and $R^5$ are independently selected from —$R^a$, —O$R^a$, —S$R^a$, —N$R^a$$R^a$, —NC(=O)$R^a$, —NS(=O)$R^a$, —NS(=O)$_2$$R^a$, halogen, cyano, haloC$_{1-6}$alkyl, —CO$_2$$R^a$, —C(=O)$R^a$, —C(=O)NH$R^a$, nitro, —S(=O)$R^a$ and —S(=O)$_2$$R^a$; $R^6$ is H, C$_{1-5}$alkyl, phenyl or haloC$_{1-6}$alkyl.

In one embodiment of the previos method $L^1$ is —C(=O)—; and $R^1$ has the structure:

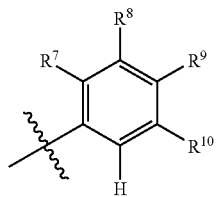

wherein: $R^7$ is H, Cl or methyl; $R^8$ is Br, Cl, F, $R^a$, O$R^a$ or allyl; $R^9$ is H, OH, NH$_2$, Br or Cl; and $R^{10}$ is H or methyl; or $R^8$ and $R^9$ combine to form —OCH$_2$O—.

In another embodiment, $R^4$ is —OH.

In another embodiment, the ligand has the structure

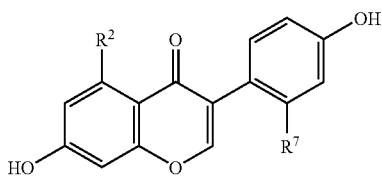

wherein $R^2$ is selected from —SCH$_3$, halogen, cyano and halo C$_{1-3}$ alkyl; and $R^7$ is selected from H, halogen and CH$_3$.

In another embodiment, the disease to be treated is selected from Alzheimer's disease, anxiety disorders, depressive disorders, osteoporosis, cardiovascular disease, rheumatoid arthritis and prostate cancer.

Another aspect of the invention relates to a composition for the treatment or prophylaxis of a disease associated with the estrogen receptor-β, comprising: a therapeutically-effective amount of a ligand that satisfies the equation:

$$K_{i\alpha A}/K_{i\beta A} > 25,$$

wherein $K_{i\alpha A}$ the $K_i$ value for the ligand in ER-α; $K_{i\beta A}$ is the $K_i$ value for the ligand in ER-β; the ligand also having the structure

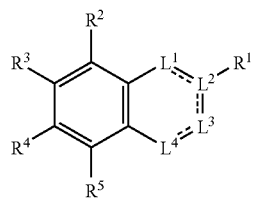

wherein: $L^1$ is —C(=O)—, =C($R^6$)—, —CH($R^6$)—, O, S, or N$R^a$; $L^2$ is =C— or —CH—; $L^3$ is =C($R^6$)—, —CH($R^6$)— or —C(=O)—; $L^4$ is —C(=O)—, CH$_2$, O, S, or N$R^a$; wherein: when $L^1$ is —C(=O)—, $L^4$ is CH$_2$, O, S, or N$R^a$; when $L^4$ is —C(=O)—, $L^1$ is CH$_2$, O, S, or N$R^a$; when $L^3$ is —C(=O)—, $L^1$ is =C($R^6$)— or —CH($R^6$)—, and $L^4$ is O or N$R^a$; when $L^1$ is =C($R^6$)—, $L^2$ is =C—; when $L^1$ is —CH($R^6$)—, $L^2$ is —CH—; when $L^3$ is =C($R^6$)—, $L^2$ is =C—; and when $L^3$ is —CH($R^6$)—, $L^2$ is —CH—; $R^a$ is, independently, at each occurrence, H or (C$_1$–C$_5$)alkyl; $R^1$ is phenyl, substituted phenyl or Het; $R^2$ is selected from —S$R^a$, —N$R^a$$R^a$, —NC(=O)$R^a$, —NS(=O)$R^a$, —NS(=O)$_2$$R^a$, halogen, cyano, haloC$_{1-6}$alkyl, —CO$_2$$R^a$, —C(=O)$R^a$, —C(=O)NH$R^a$, nitro, —S(=O)$R^a$ and —S(=O)$_2$$R^a$; $R^3$, $R^4$ and $R^5$ are independently selected from —$R^a$, —O$R^a$, —S$R^a$, —N$R^a$$R^a$, —NC(=O)$R^a$, —NS(=O)$R^a$, —NS(=O)$_2$$R^a$, halogen, cyano, haloC$_{1-6}$alkyl, —CO$_2$$R^a$, —C(=O)$R^a$, —C(=O)NH$R^a$, nitro, —S(=O)$R^a$ and —S(=O)$_2$$R^a$; $R^6$ is H, C$_{1-5}$alkyl, phenyl or haloC$_{1-6}$alkyl; and any pharmaceutically-acceptable salt thereof; and a pharmaceutically-acceptable diluent or carrier.

In another embodiment of the composition $L^1$ is —C(=O)—; and $R^1$ has the stucture:

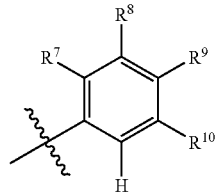

wherein: $R^7$ is H, Cl or methyl; $R^8$ is Br, Cl, F, $R^a$, O$R^a$ or allyl; $R^9$ is H, OH, NH$_2$, Br or Cl; and $R^{10}$ is H or methyl; or $R^8$ and $R^9$ combine to form —OCH$_2$O—.

In another embodiment, $R^4$ is —OH.

In another embodiment, the ligand has the structure

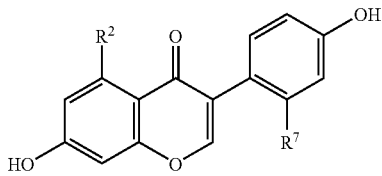

wherein $R^2$ is selected from —$SCH_3$, halogen, cyano and halo$C_{1-3}$alkyl; and $R^7$ is selected from H, halogen and $CH_3$.

In another embodiment of the composition, the disease to be treated is selected from Alzheimer's disease, anxiety disorders, depressive disorders, osteoporosis, cardiovascular disease, rheumatoid arthritis and prostate cancer.

Another aspect of the invention relates to the manufacture of a medicament for the treatment or prophylaxis of a disease associated with the estrogen receptor-β, comprising: a therapeutically-effective amount of a ligand that satisfies the equation:

$K_{i\alpha A}/Ki_{\beta A}>25$, wherein $K_{i\alpha A}$ is the $K_i$ value for the ligand in ER-α; $K_{i\beta A}$ is the $K_i$ value for the ligand in ER-β; the ligand also having the structure:

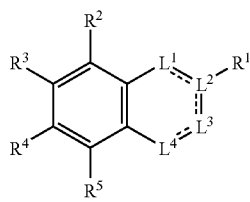

wherein:
$L^1$ is —C(=O)—, =C($R^6$)—, —CH($R^6$)—, O, S, or NR$^a$; $L^2$ is =C— or —CH—; $L^3$ is =C($R^6$)—, —CH($R^6$)— or —C(=O)—; $L^4$ is —C(=O)—, $CH_2$, O, S, or NR$^a$; wherein: when $L^1$ is —C(=O)—, $L^4$ is $CH_2$, O, S, or NR$^a$; when $L^4$ is —C(=O)—, $L^1$ is $CH_2$, O, S, or NR$^a$; when $L^3$ is —C(=O)—, $L^1$ is =C($R^6$)— or —CH($R^6$)—, and $L^4$ is O or NR$^a$; when $L^1$ is =C($R^6$)—, $L^2$ is =C—; when $L^1$ is —CH($R^6$)—, $L^2$ is —CH—; when $L^3$ is =C($R^6$)—, $L^2$ is =C—; and when $L^3$ is —CH($R^6$)—, $L^2$ is —CH—; $R^a$ is, independently, at each occurrence, H or $(C_1-C_5)$alkyl; $R^1$ is phenyl, substituted phenyl or Het; $R^2$ is selected from —SR$^a$, —NR$^a$R$^a$, —NC(=O)R$^a$, —NS(=O)R$^a$, —NS(=O)$_2$R$^a$, halogen, cyano, halo$C_{1-6}$alkyl, —CO$_2$R$^a$, —C(=O)R$^a$, —C(=O)NHR$^a$, nitro, —S(=O)R$^a$ and —S(=O)$_2$R$^a$; $R^3$, $R^4$ and $R^5$ are independently selected from —R$^a$, —OR$^a$, —SR$^a$, —NR$^a$R$^a$, —NC(=O)R$^a$, —NS(=O)R$^a$, —NS(=O)$_2$R$^a$, halogen, cyano, halo$C_{1-6}$alkyl, —CO$_2$R$^a$, —C(=O)R$^a$, —C(=O)NHR$^a$, nitro, —S(=O)R$^a$ and —S(=O)$_2$R$^a$; $R^6$ is H, $C_{1-5}$alkyl, phenyl or halo$C_{1-6}$alkyl; and any pharmaceutically-acceptable salt thereof; and a pharmraceutically-acceptable duluent or carrier.

In another embodiment of the manufacture of a medicament $L^1$ is —C(=O)—; and $R^1$ has the structure:

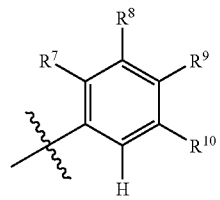

wherein: $R^7$ is H, Cl or methyl; $R^8$ is Br, Cl, F, R$^a$, OR$^a$ or allyl; $R^9$ is H, OH, $NH_2$, Br or Cl; and $R^{10}$ is H or methyl; or $R^8$ and $R^9$ combine to form —OCH$_2$O—.

In another embodiment, $R^4$ is —OH.

In another embodiment, the ligand has the structure

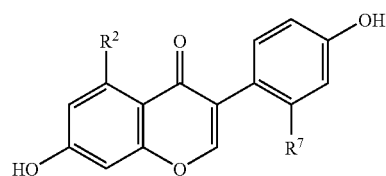

wherein $R^2$ is selected from —$SCH_3$, halogen, cyano and halo$C_{1-3}$alkyl; and $R^7$ is selected from H, halogen and $CH_3$.

In one embodiment of manufacture of a medicament the disease to be treated is selected from Alzheimer's disease, anxiety disorders, depressive disorders, osteoporosis, cardiovascular disease, rheumatoid artritis and prostate cancer.

Another aspect of the invention is novel compounds having the structure

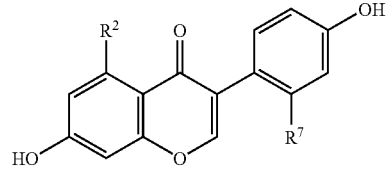

wherein $R^2$ is selected from —$SCH_3$, halogen, cyano and halo$C_{1-3}$alkyl; and $R^7$ is selected from H, halogen and $CH_3$.

In one embodiment, $R^2$ halogen; and $R^7$ is H.

Halo$C_{1-6}$alkyl means a branched, cyclic or strait-chain alkyl group having from 1 to 6 carbon atoms, substituted with at least one halogen atom (Br, Cl, F, I). The alkyl group may contain mixed halogens, but the total number of halogen atoms shall not exceed the number of valences on the alkyl group that are normally occupied by hydrogens. One specific example is $CF_3$.

Pharmaceutically-acceptable salts may be prepared from the corresponding acid in conventional manner. Non-pharmaceutically-acceptable salts may be useful as intermediates and as such are another aspect of the present invention.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium sales, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Estrogen Receptor Binding Measurements

The ability of a compound to bind to ER was measured by its ability to compete for binding with the radio-labeled estrogen, [$^{125}$I]-16α-iodo-3,17β-estradiol (NEN, Cat.#NEX-144). The radio-ligand is hereafter referred to as [$^{125}$I]-estradiol.

ER-β (Gen Bank Accession #X99101) or ER-α (Gen Bank Accession #M12674) cDNAs were cloned into the expression vector pSG5 (Stratagene), transformed into e. coli strain DHαF', and purified using anion-exchange resin columns (Qiagen Cat.#12125). Receptor protein was prepared by in vitro transcription and translation of these plasmids using the TNT T7 Quick-Coupled reticulocyte lysate system (Promega Cat.#L1170). Reticulocyte lysate (12.5 mL) was incubated for 90 min at 30° C. with 312.5 μg of ER-α and 625 μg of ER-β plasmids. Programmed lysate was then aliquotted and stored frozen at –80° C.

Compounds were tested in duplicate at half-log concentrations ranging from 10 pM to 3 μM. Compounds were prepared as 1 mM stocks in DMSO, then diluted in the binding-assay buffer (in mM: 20 HEPES, 150 NaCl, 1 EDTA, 6 monothioglycerol and 10 $Na_2MoO_4$,; 10% wt/vol glycerol, and pH=7.9) to a series of three-fold concentrated, 20 μL aliquots in a 96-well plate. Receptor aliquots were thawed on ice, and appropriately diluted (see below) in binding assay buffer. Diluted receptor (30 μL/each) was added to each well. [$^{125}$I]-estradiol was diluted from the manufacturer's ethanol stock solution to a 900 pM working solution in binding-assay buffer. The final assay volume was 60 μL, consisting of 20 μL of a compound according to the instant invention, 30 μL of programmed reticulocyte lysate, and 10 μL of 900 pM [$^{125}$I]-estradiol. The final concentration of [$^{125}$I]-estradiol was 150 pM. Plates containing the final assay mixture were mixed on a shaker for 2 min and incubated overnight (~16 h) at 4° C.

Receptor-bound and unbound radioligand was separated by filtration over sephadex columns. Columns (45 μL bed volume) were prepared by adding dry column media (Pharmacia Cat#G-25) to 96-well column templates (Millipore MultiScreen Plates Cat#MAHVN4510). Columns were then saturated with 300 μL of binding-assay buffer and stored at 4° C. Prior to use, stored columns were spun for 10 minutes at 2000 RPM, then washed twice with 200 μL of fresh binding buffer. The binding-assay mixtures (50 μL/each) were then applied to the columns, and an additional elution volume of 35 μL was immediately applied to the column. Receptor-bound radioligand was then eluted from the column by centrifugation for 10 minutes at 2000 RPM. A scintillation cocktail (145 μL) was added to the eluted radioligand/receptor complex, and radio-label was measured by liquid scintillation counting.

Non-specific binding was defined by competition with 150 nM diethylstilbesterol (DES). Binding affinities are expressed as $K_i$, calculated using the Cheng-Prushoff formula according to $IC_{50}$ values generated by fitting the relationship of concentration to percent specific binding (SB) with the following equation:

$$\% \text{ SB} = \text{Maximum} - (\text{Maximum} - \text{Minimum}) / (1 + 10^{(logIC50 - log[Compound])})$$

In this assay, standard estrogen receptor ligands estradiol and DES were detected as high-affinity ($K_i$<1 nM), non-selective ligands of ERP and ER-α.

The volume of receptor-programmed reticulocyte lysate to be added to the binding assay was determined independently from two measurements made on each batch of receptor prepared. First, $K_i$s were determined for standard compounds using a series of dilutions of the receptor preparation. Scatchard analysis of ligand binding affinity was performed at the receptor dilutions that produced reported $K_i$s for these compounds and an acceptable signal:noise ratio (~10). These experiments indicated a $K_D$ for [$^{125}$I]-estradiol of 0.1–1 nM, and a $B_{max}$ of 5–30 pmol.

Administration and Use

Compounds of the present invention are shown to have high selectivity for ER-β over ER-α, and may possess agonist activity on ER-β without undesired uterine effects. Thus, these compounds, and compositions containing them, may be used as therapeutic agents in the treatment of various CNS diseases related to ER-β, such as, for example, Alzheimer's disease.

The present invention also provides compositions comprising an effective amount of compounds of the present invention, including the nontoxic addition salts, amides and esters thereof, which may, serve to provide the above-recited therapeutic benefits. Such compositions may also be provided together with physiologically-tolerable liquid, gel or solid diluents, adjuvants and excipients. The compounds of the present invention may also be combined with other compounds known to be used as therapeutic agents for the above or other indications.

These compounds and compositions may be administered by qualified health care professionals to humans in a manner similar to other therapeutic agents and, additionally, to other mammals for veterinary use, such as with domestic animals. Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders.

The present compounds may be formulated into the compositions as neutral or salt forms. Pharmaceutically-acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention that display ER-β activity, compounds of the present invention can also be employed as intermediates in the synthesis of such useful compounds.

Synthesis

Compounds within the scope of the present invention may be synthesized chemically by means well known in the art. The following Examples are meant to show general synthetic schemes, which may be used to produce many different variations by employing various commercially-available starting materials. These Examples are meant only as guides on how to make some compounds within the scope of the invention, and should not be interpreted as limiting the scope of the invention.

EXAMPLES

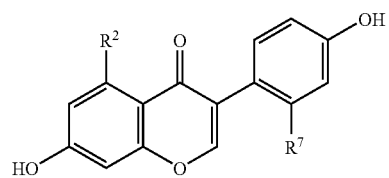

| Example | $R^2$ | $R^7$ | FP β-ER $K_i$ (nM) | FP α-ER $K_i$ (nM) | Selectivity |
|---|---|---|---|---|---|
| 1 | Cl | H | 4.3 | 600 | 139 |
| 2 | Cl | Cl | 16 | 300 | 19 |
| 3 | Cl | Me | 50 | 900 | 18 |
| 4 | F | H | 39 | >2200 | >56 |
| 5 | Br | H | 2.8 | 251 | 90 |
| 6 | I | H | 3.9 | 147 | 38 |
| 7 | CN | H | 58 | >1000 | >39 |
| 8 | SMe | H | 84 | 563 | 7 |

| Example | Structure | FP β-ER $K_i$ (nM) | FP α-ER $K_i$ (nM) | Selectivity |
|---|---|---|---|---|
| 9 | 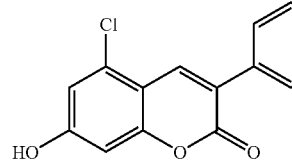 | 1.8 | 62 | 35 |
| 10 | 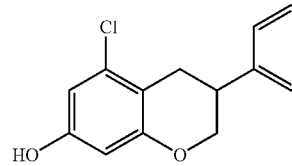 | 2.0 | 13 | 6.4 |

The HPLC conditions used are the following unless stated otherwise: HPLC 2.1×50 mm $C_8$ 5 µm Zorbax Stablebond column; flow rate 1.4 mL/min, linear gradient from 15% B to 90% B over 4.0 mm; A=water, 0.05% TFA; B=90% acetonitrile, 10% water, 0.05% TFA, UV detection at 254 nm and positive ionization mass spectrometry detection.
DMF=N,N-dimethylformamide
THF=tetrahydrofuran
TFA=trifluoroacetic acid
DMSO=dimethylsulfoxide Example 1

5-Chloro-7-hydroxy-3-(4-hydroxyphenyl)-4-oxo-4H-1 benzopyran

1) Synthesis of 2-chloro-4,6-dihydroxyacetophenone

To a solution of 2-chloro-6-hydroxy-4 methoxyacetophenone [1] (23.7 g, contaminated with 4-chloro-2-hydroxy-6-methoxyacetophenone) in dichloromethane (100 mL) cooled at −78° C. was added boron tribromide (1M solution in dichloromethane, 200 mL). The mixture was stirred at room temperature for two days, cooled at 0° C. and poured into ice water. Dichloromethane was evaporated in vacuo and the resulting solution was filtered. The solids were washed with ethyl acetate several times and discarded. The filtrates were extracted with ethyl acetate. The organic layer was washed with brine and dried over $MgSO_4$ to give crude 2-chloro-4,6-dihydroxyacetophenone as a brown solid (19 g). $^1$H NMR ($CDCl_3$): 13.38 (s, 1H), 6.52 (d, 1H, J=2.4 Hz), (d, 1H, J=2.4 Hz), 5.63 (s br, 1H), 2.81 (s, 3H).

Ref. 1: made according to European Patent Application EP0248420

2) Synthesis of 2-chloro-6 hydroxy-4-(2-trimethysilylethoxymethoxy)acetophenone

To a solution of 2-chloro-4,6-dihydroxyacetophenone (10.27 g) in DMF (100 mL) at 0° C. was added diisopropylethylamine (20 mL) and trimethylsilylethoxymethyl chloride (12.8 mL) drop-wise. The mixture was stirred for three days, poured into water and extracted with hexane. The organic layer was washed with brine and dried over $MgSO_4$. Chromatography on silica gel (eluant: 10% ether in hexane) gave the title compound (6 g) contaminated with an unknown material. MS: 315(M-H$^-$).

3) Synthesis of 1-[2-chloro-6-hydroxy-4-(2-trimethylsilylethoxymethoxy)phenyl]-3-dimethylamino-2-propen-1-one A solution of the compound obtained above (6.56 g) in dimethylformamide dimethylacetal (9 mL) was heated under nitrogen at 70° C. for 2 h. The solvents were evaporated in vacuo. Chromatography on silica gel (eluant: 3% ethyl acetate in dichloromethane) gave the title compound (2.1 g). MS: 372 (MH$^+$); HPLC $t_R$: 2.57 min.

4) Synthesis of 5-chloro-3-iodo-7-(2-trimethylsilylethoxymethoxy)-4-oxo-4H-1-benzopyran To a solution of the above compound (2.1 g) in chloroform (50 mL) at room temperature was added a solution of iodine (3.02 g) in toluene (35 mL) drop-wise over 5 min. The mixture was stirred at room temperature for 30 min. A 10% aqueous solution of sodium bisulfite was added and the mixture was stirred vigorously for 5 min. The mixture was extracted with dichloromethane. The organic layer was dried over $MgSO_4$ and purified by chromatography on silica gel (eluant: ethyl acetate-dichloromethane-hexane 5:25:70) to afford the title compound (1.65 g) as a white solid. $^1$H NMR ($CDCl_3$): 8.13 (s, 1H), 7.13 (d, 1H, J=2.4 Hz), 6.99 (d, 1H, J=2.4 Hz), 5.28 (s, 2H), 3.76 (t, 2H, J=8.2 Hz), 0.95 (t, 2H, J=8.2 Hz), 0.0 (s, 9H); MS: 475 (MNa$^+$). Synthetic method A:

5) Synthesis of 5-chloro-3-(4-tert-butyldimethylsilyloxyphenyl)-7-(2-trimethylsilylethoxy-methoxy)-4-oxo-4H-1-benzopyran To a solution of the above compound (300 mg), 4-(tert-butyldimethylsilyloxy)-phenylboronic acid (215 mg) [2] and silver oxide (243 mg) in THF (5 mL)-water (0.5 mL) under nitrogen were added triphenylarsine (22 mg) and bis(benzonitrile)dichloropalladium(II) (13 mg). The mixture was stirred vigorously at room temperature for two days, diluted with ethyl acetate and dried on $MgSO_4$. After filtration and evaporation of the solvents, the residue was chromatographed on a 10 g Varian Bond Elute silica gel column (eluant: gradient from hexane to 2% ethyl acetate −40% dichloromethane-hexane) to give the title compound (200 mg) as a colorless oil. MS: 533 (MH$^+$).

Ref. 2: UK patent GB2276162 (1994)

6) Synthesis of 5-chloro-7-hydroxy-3-(4-hydroxyphenyl)-4-oxo-4H-1-benzopyran

To methanol (10 mL) cooled at 0° C. was added acetyl chloride (0.7 mL) drop-wise. The mixture was stirred at 0° C. for 15 min. To this solution was added the above compound (300 mg) in dichloromethane (10 mL). The mixture was stirred at room temperature for 6 h. The solvents were evaporated in vacuo. The residue was triturated with ether-hexane to give the title compound as a white powder (119 mg). $^1$H NMR (DMSO-$d_6$): 11.10 (s br, 1H), 9.49 (s br, 1H), 8.20 (s, 1H), 7.32 (d, 2H, J=8.4 Hz), 6.92 (d, 1H, J=2.1 Hz), 6.84 (d, 1H, J=2.1 Hz), 6.79 (d, 2H, J=8.4 Hz); MS: 289 (MH$^+$).

Examples 2 and 3

5-Chloro-3-(2-chloro-4-hydroxyphenyl)-7-hydroxy-4-oxo-4H-1-benzopyran and 5-chloro-7-hydroxy-3-(4-hydroxy-2-methylphenyl)-4-oxo-4H-1-benzopyran Similarly, using method A, respectively from 4-(tert-butyldimethylsilyloxy)-2-chlorophenylboronic acid and 4-(tert-butyldimethylsilyloxy)-2-methylphenylboronic acid [obtained respectively from 4-bromo-3-chlorophenol and 4-bromo-3-methylphenol by a) silylation with tert-butyldimethylsilyl chloride and triethylamine in DMF, b) lithium-halogen exchange with n-butyllithium (1 eq.) at −78° C. in THF and trapping of the anion with triisopropylborate according to ref. 2] were obtained: 5-chloro-3-(2-chloro-4-hydroxyphenyl)-7-hydroxy-4-oxo-4H-1-benzopyran; $^1$H NMR (DMSO-$d_6$): 11.18 (m, 1H), 9.98 (m, 1H), 8.16 (s, 1H), 7.15 (d, 1H, J=8.4 Hz), 6.94 (d, 1H, J=2.1 Hz), 6.91 (d, 1H, J=2.1 Hz), 6.87 (d, 1H, J=2.1 Hz), 6.78 (dd, 1H, J=8.4 Hz, J'=2.1 Hz); MS: 323 (MH$^+$) and 5-chloro-7-hydroxy-3-(4-hydroxy-2-methylphenyl)-4-oxo-4H-1-benzopyran; $^1$H NMR (DMSO-$d_6$): 11.10 (s, 1H), 9.35 (s br, 1H), 8.05 (s, 1H), 6.92 (m, 2H), 6.85 (d, 1H, J=2.1 Hz), 6.66 (s br, 1H), 6.60 (d br, 1H, J=8.1 Hz), 2.05 (s, 3H); MS: 303 (MH$^+$).

Example 4

5-Fluoro-7-hydroxy-3-(4-hydroxyphenyl)-4-oxo-4H-1-benzopyran

1) Synthetic method B: Synthesis of 1-(2-fluoro-6-hydroxy-4-methoxyphenyl)-2-(4-methoxyphenyl)ethanone To 1,2-dichloroethane (40 mL) were added anhydrous aluminum chloride (4.27 g) and zinc chloride (436 mg), followed by stirring 15 min. Under ice-cooling, a solution of 1,3-dimethoxy-5-fluorobenzene (5 g) in 1,2-dichloroethane (15 mL) was added. The mixture was cooled to −10° C. and 4-methoxyphenylacetyl chloride (4.9 mL) in dichloroethane (10 mL) was added drop-wise. The mixture was stirred 30 min at −10° C., and 1 h at room temperature and then heated to reflux for 2 h. The mixture was cooled at 0° C., poured carefully into ice-water and extracted twice with dichloromethane. The dichloromethane layer was dried over MgSO$_4$ and evaporated in vacuo to give the title compound (9.1 g); $^1$H NMR (CDCl$_3$): 13.23 (s, 1H), 7.17 (d, 2H, J=8.4 Hz), 6.88 (d, 2H, J=8.4 Hz), 6.24 (d, 1H, J=2.1 Hz), 6.18 (dd, 1H, J=13.8 Hz, J'=2.1 Hz), 4.20 (d, 2H, J=3.9 Hz), 3.82 (s, 3H), 3.80 (s, 3H); MS: 291 (MH$^+$); containing 1-(4-fluoro-2-hydroxy-6-methoxyphenyl)-2-(4-methoxyphenyl)ethanone as a by-product. $^1$H NMR (CDCl$_3$): 13.62 (s, 1H), 7.2–6.0 (6H), 4.29 (s, 2H), 3.90 (s, 3H), 3.81 (s, 3H).

2) Synthetic method C: Synthesis of 5-fluoro-7-methoxy-3-(4-methoxyphenyl)-4-oxo-4H-1-benzopyran To a suspension of 1,1-carbonyldiimidazole (17.8 g) in THF (60 mL) cooled at 0° C. was added drop-wise formic acid (4.24 mL). After 10 min, a solution of the compound obtained above (6.42 g) in THF (60 mL) was added. The mixture was stirred 10 min at 0° C. and 72 h at room temperature. Part of the THF was evaporated and the residue was partitioned between ethyl acetate and water. The organic layer was washed with brine and dried over MgSO$_4$. Chromatography on silica gel (eluant: 2% ethyl acetate-chloroform) gave the title compound (2.87 g). $^1$H NMR (DMSO-d$_6$): 8.36 (s, 1H), 7.47 (d, 2H, J=8.4 Hz), 7.03 (s br, 1H), 6.99 (d, 2H, J=8.4 Hz), 6.93 (d br, 1H, J=13.2 Hz), 3.91 (s, 3H), 3.79 (s, 3H); MS: 301 (MH$^+$), HPLC t$_R$: 2.45 min. Further elution gave the regioisomer 7-fluoro-5-methoxy-3-(4-methoxyphenyl)-4-oxo-4H-1-benzopyran. $^1$H NMR (CDCl$_3$): 7.80 (s, 1H), 7.47 (d, 2H, J=8.7 Hz), 6.94 (d, 2H, J=8.7 Hz), 6.71 (dd, 1H, J=8.7 Hz, J'=2.1 Hz), 6.56 (dd, 1H, J=11 Hz, J'=2.1 Hz), 3.97 (s, 3H), 3.83 (s, 3H).

3) Synthetic method D: Synthesis of 5-fluoro-7-hydroxy-3-(4-hydroxyphenyl)-4-oxo-4H-1-benzopyran A mixture of 5-fluoro-7-methoxy-3-(4-methoxyphenyl)-4-oxo-4H-1-benzopyran (132 mg) and pyridine hydrochloride (2 g) in a test tube was heated in an oil bath (preheated at 200° C.). The mixture melted, was stirred at 200° C. for 40 min and cooled. The residue was poured into 1N hydrochloric acid. The solids were filtered, washed with water and ether, and dried under high vacuum to give the title compound as a beige powder (82 mg). $^1$H NMR (DMSO-d$_6$): 11.19 (s br, 1H), 9.55 (s br, 1H); 8.22 (s, 1H), 7.33 (d, 2H, J=7.8 Hz), 6.80 (d, 2H, J=7.8 Hz), 6.71 (s br, 1H), 6.65 (d br, 1H, J=12.9 Hz); MS: 273 (MH$^+$); HPLC t$_R$: 1.66 min.

Example 5

5-Bromo-7-hydroxy-3-(4-hydroxyphenyl)-4-oxo-4H-1-benzopyran

According to methods B, C and D, from 5-bromo-1,3-dimethoxybenzene [3] (5.42 g) was obtained: 1-(2-bromo-6-hydroxy-4-methoxyphenyl)-2-(4-methoxyphenyl)ethanone (0.91 g) after purification of the regioisomers by chromatography on silica gel (eluant: dichloromethane-hexane, gradient from 1:2 to 2:1). $^1$H NMR (DMSO-d$_6$): 12.55 (s, 1H), 7.13 (d, 2H, J=8.4 Hz), 6.87 (d, 2H, J=8.4 Hz), 6.82 (d, 1H, J=2.4 Hz), 6.40 (d, 1H, J=2.4 Hz), 4.53 (s, 2H), 3.81 (s, 3H), 3.79 (s, 3H); MS: 351 (MH$^+$); 5-bromo-7-methoxy-3-(4-methoxyphenyl)-4-oxo-4H-1-benzopyran (0.78 g); $^1$H NMR (DMSO-d$_6$): 8.35 (s, 1H), 7.47 (d, 2H, J=8.7 Hz), 7.33 (d, 1H, J=2.4 Hz), 7.20 (d, 1H, J=2.4 Hz), 6.98 (d, 2H, J=8.7 Hz), 3.91 (s, 3H), 3.79 (s, 3H); MS: 361 (MH$^+$); and 5-bromo-7-hydroxy-3-(4-hydroxyphenyl)-4-oxo-4H-1 benzopyran (143 mg) after aqueous work-up, and extraction with ethyl acetate; $^1$H NMR (DMSO-d$_6$): 11.08 (s, 1H), 9.50 (s, 1H), 8.22 (s, 1H), 7.32 (d, 2H, J=8.4 Hz), 7.16 (d, 1H, J=2.4 Hz), 6.88 (d, 1H, J=2.4 Hz), 6.79 (d. 2H, J=8.4 Hz); MS: 333 (MH$^+$); HPLC t$_R$: 1.80 min.

Ref 3: Detty, M. R.; Murray, B. J.; J. Am. Chem. Soc., 1983, 883

Example

7-Hydroxy-3-(4-hydroxyphenyl)-5-iodo-4-oxo-4H-1-benzopyran

1) Synthesis of 5-iodo-7-methoxy-3-(4-methoxyphenyl)-4-oxo-4H-1-benzopyran.

A suspension of 5-bromo-7-methoxy-3-(4-methoxyphenyl)-4-oxo-4H-1-benzopyran (95 mg), copper(I) iodide (250 mg) and potassium iodide (462 mg) in DMSO (6 mL) was heated at 115° C. for 2 h. The mixture was cooled, poured into 1M hydrochloric acid and extracted with ethyl acetate. The organic layer was washed with 1M hydrochloric acid and brine and dried over MgSO$_4$. Chromatography on silica gel (eluant: ethyl acetate-dichloromethane-hexane 1:10:20) afforded the title compound (95 mg). $^1$H NMR (DMSO-d$_6$): 8.40 (s, 1H), 7.63 (d, 1H, J=2.7 Hz), 7.47 (d, 2H, J=8.7 Hz), 7.22 (d, 1H, J=2.7 Hz), 6.99 (d, 2H, J=8.7 Hz), 3.90 (s, 3H), 3.79 (s, 3H); MS: 409 (MH$^+$); HPLC t$_R$: 2.83 min.

2) According to method D, from 5-iodo-7-methoxy-3-(4-methoxyphenyl)-4-oxo-4H-1-benzopyran (95 mg) was obtained 7-hydroxy-3-(4-hydroxyphenyl)-5-iodo-4-oxo-4H-1 benzopyran (75 mg) after aqueous work-up, extraction with ethyl acetate and chromatography on silica gel (eluant: 3% methanol in dichloromethane). $^1$H NMR (DMSO-d$_6$): 10.97 (s, 1H), 9.52 (s, 1H), 8.27 (s, 1H), 7.52 (d, 1H, J=2.4 Hz), 7.33 (d, 2H, J=8.4 Hz), 6.89 (d, 1H, J=2.4 Hz), 6.80 (d, 2H, J=8.4 Hz); MS: 381 (MH$^+$); HPLC t$_R$: 1.87 min.

Example 7

5-Cyano-7-hydroxy-3-(4-hydroxyphenyl)-4-oxo-4H-1-benzopyran

1) Synthesis of 5-cyano-7-methoxy-3-(4-methoxyphenyl)-4-oxo-4H-1-benzopyran.

A suspension of 5-bromo-7-methoxy-3-(4-methoxyphenyl)-4-oxo-4H-1 benzopyran (150 mg), copper(I) cyanide (55.5 mg) in DMF (4 mL) was heated at 120° C. for 3 h. The mixture was cooled, poured into cold water and extracted with ethyl acetate. The organic layer was washed with 1M hydrochloric acid, saturated aqueous sodium bicarbonate and brine, and dried over MgSO$_4$. Evaporation of the solvents afforded the title compound (126 mg) as a white solid. $^1$H NMR (DMSO-d$_6$): 8.52 (s, 1H), 7.67 (d, 1H, J=2.7 Hz), 7.54 (m, 3H), 7.01 (d, 2H, J=8.7 Hz), 3.97 (s, 3H), 3.80 (s, 3H); MS: 308 (MH$^+$); HPLC t$_R$: 2.29 min.

2) According to method D, from 5-cyano-7-methoxy-3-(4-methoxyphenyl)-4-oxo-4H-1-benzopyran (160 mg) was obtained 5-cyano-7-hydroxy-3-(4-hydroxyphenyl)-4-oxo-4H-1 benzopyran (140 mg). $^1$H NMR (DMSO-d$_6$): 11.48 (s, 1H), 9.58 (s, 1H), 8.39 (s, 1H), 7.38 (m, 3H), 7.19 (d, 1H, J=2.4 Hz), 6.82 (d, 2H, J=6.9 Hz); MS: 280 (MH$^+$); HPLC t$_R$: 1.64 min.

Example 8

7-Hydroxy-3-(4-hydroxyphenyl)-5-methylthio-4-oxo-4H-1-benzopyran

1) Synthesis of 7-methoxy-3-(4-methoxyphenyl)-5-methylthio-4-oxo-4H-1-benzopyran.

Sodium thiomethoxide (600 mg) was added to a solution of 5-fluoro-7-methoxy-3-(4-methoxyphenyl)-4-oxo-4H-1-benzopyran (325 mg) in THF (10 mL). The mixture was refluxed for 1 h and cooled. The mixture was partitioned between ethyl acetate and water. The organic layer was washed with water and brine, and dried over MgSO$_4$. Purification by chromatography on silica gel (eluant: ethyl acetate-chloroform, gradient from 0:100 to 5:95) gave the title compound (310 mg) as a pale yellow solid. $^1$H NMR (CDCl$_3$): 7.81 (s, 1H), 7.50 (d, 2H, J=8.7 Hz), 6.95 (d, 2H, J=8.7 Hz), 6.67 (d, 1H, J=2.1 Hz), 6.59 (d, 1H, J=2.1 Hz), 3.91 (s, 3H), 3.83 (s, 3H); MS: 329 (MH$^+$); HPLC t$_R$: 2.68 min.

2) According to method D, from 7-methoxy-3-(4-methoxyphenyl)-5-methylthio-4-oxo-4H-1-benzopyran (108 mg) was obtained 7-hydroxy-3-(4-hydroxyphenyl)-5-methylthio-4-oxo-4H-1-benzopyran (53 mg). $^1$H NMR (DMSO-d$_6$): 10.76 (s, 1H), 9.51 (s, 1H), 8.16 (s, 1H), 7.33 (d, 2H, J=8.7 Hz), 6.80 (d, 2H, J=8.7 Hz), 6.64 (d, 1H, J=1.8 Hz), 6.58 (d, 1H, J=1.8 Hz), 2.34 (s, 3H); MS: 301 (MH$^+$); HPLC t$_R$: 1.85 min.

Example 9

5-Chloro-7-hydroxy-3-(4-hydroxyphenyl)coumarin

1) Synthesis of 2-chloro-6-hydroxy-4-methoxybenzaldehyde.

To a solution of 2-chloro-4,6-dimethoxybenzaldehyde [4] (3.15 g) in dichloromethane (30 mL) cooled at –78° C. was added boron tribromide (1M solution in dichloromethane, 16 mL). The mixture was stirred at –78° C. for 30 min, warmed and stirred at room temperature for 18 h. The mixture was cooled to 0° C., poured into ice-water and extracted with ethyl acetate. The organic layer was washed with brine and dried over MgSO$_4$. Evaporation of the solvent gave the title compound (2.85 g). $^1$H NMR (DMSO-d$_6$): 12.15 (s, 1H), 10.14 (s, 1H), 6.74 (d, 1H, J=2.1 Hz), 6.53 (d, 1H, J=2.1 Hz), 3.86 (s, 3H).

Ref. 4: Sargent, M. V.; J. Chem. Soc. Perkin Trans 1, 1982, 1095

2) Synthesis of 5-chloro-7-methoxy-3-(4-methoxyphenyl) coumarin

A solution of 2-chloro-6-hydroxymethoxybenzaldehyde (2.85 g), 4-methoxyphenylacetic acid (2.54 g) and sodium acetate (3 g) in acetic anhydride (25 mL) was refluxed for 18 h and cooled. Cold water (200 mL) was added. The solids were filtered, washed with water (three times) and ether-hexane (1:1), and dried under high vacuum to give the title compound (2.92 g). $^1$H NMR (DMSO-d$_6$): 8.03 (s, 1H), 7.68 (d, 2H, J=8.7 Hz), 6.98 (d, 2H, J=8.7 Hz), 6.94 (d, 1H, J=1.8 Hz), 6.77 (d, 1H, J=1.8 Hz), 3.87 (s, 6H).

3) According to method D, from 5-chloro-7-methoxy-3-(4-methoxyphenyl)coumarin was obtained 5-chloro-7-hydroxy-3-(4-hydroxyphenyl)coumarin: $^1$H NMR (DMSO-d$_6$): 10.98 (s, 1H), 9.73 (s, 1H), 7.91 (s, 1H), 7.55 (d, 2H, J=8.4 Hz), 6.94 (d, 1H, J=1.8 Hz), 6.84 (d, 2H, J=8.4 Hz), 6.75 (d, 1H, J=1.8 Hz); MS: 289 (MH$^+$); HPLC t$_R$: 2.04 min.

Example 10

5-Chloro-7-hydroxy-3-(4 hydroxyphenyl)chroman

1) Synthesis of 7-(tert-butyldimethylsilyloxy)-3-[4-(tert-butyldimethylsilyloxy)phenyl]5-chlorocoumarin To a solution of 5-chloro-7-hydroxy-3-(4-hydroxyphenyl) coumarin (1.15 g) in DMF (10 mL) at room temperature were added imidazole (800 mg) and tert-butyldimethylsilyl chloride (1.6 g). The mixture was stirred for 18 h, poured into water and extracted with ether. The organic layer was washed with water and brine, and dried over MgSO$_4$. Chromatography on silica gel (eluant: 10% ether in hexane) gave the title compound as a pale yellow oil (1.81 g) crystallizing on standing. MS: 517 (MH$^+$).

2) Synthesis of 7-(tert-butyldimethylsilyloxy)-3-[4-(tert-butyldimethylsilyloxy)phenyl]-5-chloro-2-hydroxy-2H-chromene To a solution of the compound obtained above (1.60 g) in THF (20 mL) cooled at –78° C. was added diisobutylaluminum hydride (1M solution in toluene, 4.6 mL) drop-wise. The mixture was stirred at –78° C. for 1 h. Water (1 mL) was added drop-wise at –78° C. The mixture was warmed to 0° C. and anhydrous sodium sulfate was added. The mixture was vigorously stirred and then diluted with ethyl acetate. The solids were filtered and washed with ethyl acetate. The solvent of the filtrate was evaporated in vacuo and the residue was chromatographed on silica gel (eluant: 10% ether in hexane) to give the title compound (1.35 g) as an oil. $^1$H NMR (CDCl$_3$): 7.50 (d, 2H, J=8.7 Hz), 7.21 (s, 1H), 6.87 (d, 2H, J=8.7 Hz), 6.60 (d, 1H, J=2.4 Hz), 6.48 (d, 1H, J=2.4 Hz), 6.23 (d, 1H, J=8.4 Hz), 2.99 (d, 1H, J=8.4 Hz), 0.99 (s, 18H), 0.22 (s, 12 H).

3) Synthesis of 7-(tert-butyldimethylsilyloxy)-3-[4-(tert-butyldimethylsilyloxy)phenyl]-5-chloro-2H-chromene In a flask equipped with a Dean-Stark condenser, a solution of the compound obtained above (1.17 g) and phenol (1.2 g) in toluene (30 mL) was heated under reflux for 3 h. The solution was cooled, partitioned between ether (50 mL) and 10% aqueous sodium carbonate. The organic layer was washed with 10% aqueous sodium carbonate, water and brine, and dried over sodium sulfate. After evaporation of ether in vacuo in a cold bath, the toluene solution of crude 7-(tert-butyldimethylsilyloxy)-3-[4-(tert-butyldimethylsilyloxy)phenyl]-5-chloro-2-phenoxy-2H-chromene was cooled at −78° C. under nitrogen. Diisobutylaluminum hydride (1M solution in toluene, 7.5 mL) was added drop-wise. The mixture was stirred at −78° C. for 1 h. Water (1 mL) was added drop-wise at −78° C. The mixture was warmed to 0° C. and anhydrous sodium sulfate was added. The mixture was vigorously stirred and then diluted with ethyl acetate. The solids were filtered and washed with ethyl acetate. The solvent of filtrate was evaporated in vacuo and the residue was chromatographed on silica gel (eluant: 10% dichloromethane in hexane) to give the title compound (380 mg) as an oil. $^1$H NMR (CDCl$_3$): 7.33 (d, 2H, J=8.7 Hz), 6.99 (s, 1H), 6.86 (d, 2H, J=8.7 Hz), 6.49 (d, 1H, J=2.1 Hz), 6.29 (d, 1H, J=2.1 Hz), 5.07 (s, 2H), 0.99 (s, 9H), 0.98 (s, 9H), 0.22 (s, 12 H); MS: 503 (MH$^+$).

4) Synthesis of 5-chloro-7-hydroxy-3-(4 hydroxyphenyl)-2H-chromene

To a solution of the compound obtained above (125 mg) in THF (2 mL) was added tetrabutylammonium fluoride (1M solution in THF, 1 mL). The mixture was stirred at room temperature for 2 h. The mixture was diluted with ethyl acetate, washed with saturated aqueous ammonium chloride, water and brine, and dried over MgSO$_4$. Chromatography on a 10 g Varian Bond Elute silica gel column (eluant: ethyl acetate-hexane, gradient from 0:100 to 30:70) gave the title compound (70 mg). $^1$H NMR (DMSO-d$_6$): 9.98 (s br, 1H), 9.64 (s br, 1H), 7.37 (d, 2H, J=8.7 Hz), 6.84 (s, 1H), 6.80 (d, 2H, J=8.7 Hz), 6.45 (d, 1H, J=2.4 Hz), 6.26 (d, 1H, J=2.4 Hz), 5.05 (s, 2H); MS: 273 (M-H$^−$).

5) Synthesis of 5-chloro-7-hydroxy-3-(4-hydroxyphenyl) chroman

To a solution of the compound obtained above (60 mg) in ethyl acetate (20 mL) was added 5% palladium on charcoal (80 mg). The suspension was stirred at room temperature under a 30 PSI atmosphere of hydrogen for 30 min. Filtration of the catalyst and evaporation of the solvent afforded the title compound after purification on a 10 g Varian Bond Elute silica gel column (eluant: ethyl acetate-hexane, gradient from 0:100 to 25:75). $^1$H NMR (CDCl$_3$): 7.12 (d, 2H, J=8.4 Hz), 6.83 (d, 2H, J=8.4 Hz), 6.53 (d, 1H, J=2.7 Hz), 6.30 (d, 1H, J=2.7 Hz), 4.83 (m, 2H), 4.27 (m, 1H), 3.92 (dd, 1H, J=J'=10.5 Hz), 3.13 (m, 1H), 3.07 (m, 1H), 2.75 (dd, 1H, J=16.2 Hz, J'=10.5 Hz); MS: 275 (M-H$^−$).

Example 11

5-Chloro-7-hydroxy-3-(4-hydroxyphenyl)-4-oxo-4H-1-benzopyran

1) Synthesis of 1-(2-chloro-4,6-dimethoxyphenyl)-2-(4-methoxyphenyl)ethanone.

To 1,2-dichloroethane (500 mL) were added anhydrous aluminum chloride (50.5 g) and zinc chloride (5.72 g), followed by stirring for 15 min. Under ice-cooling, a solution of 1,3-dimethoxy-5-chlorobenzene (55 g) in 1,2-dichloroethane (140 mL) was added. The mixture was cooled to −25° C. and 4-methoxyphenylacetyl chloride (53.9 mL) in 1,2-dichloroethane (250 mL) was added drop-wise. The mixture was allowed to warm to room temperature and stirred for 12 h. The mixture was cooled to 0° C., quenched with 1.0 N HCl (300 mL), and the resulting suspension was filtered through Celite and silica gel using ethyl acetate. Chromatography on silica gel (eluant: 10–40% ethyl acetate/hexane) provided the title compound (39 g). $^1$H NMR (DMSO-d$_6$): 7.07 (d, 2H, J=8.77 Hz), 6.85 (d, 2H, J=8.77 Hz), 6.62 (m, 2H), 3.94 (s, 2H), 3.80 (s, 6H), 3.72 (s, 3H); MS: 321 (MH$^+$).

2) Synthesis of 1-(2-chloro-4,6-dihydroxyphenyl)-2-(4-hydroxyphenyl)ethanone.

Boron tribromide (1.0 M soultion in dichloromethane, 5 mL) was added drop-wise to a solution of 1-(2-chloro-4,6-dimethoxyphenyl)-2-(4-methoxyphenyl)ethanone (1.34 g) in 1,2-dichloroethane (25 mL). The solution was heated to 70° C. for 24 h, cooled to room temperature and stirred for 90 h. Additional boron tribromide (1.0 M solution in dichloromethane, 5 mL) was added drop-wise, heating to 70° C. for 12 h. The solution was cooled to −45° C., quenched with methanol (45 mL) and concentrated in vacuo. The solids were redissolved in ethyl acetate (40 mL) and washed with saturated sodium bicarbonate (2×25 mL), 1.2 N HCl (2×25 mL) and brine (2×25 mL), dried over Na$_2$SO$_4$, filtered and concentrated in vacuo. The resulting oil was triturated with dichloromethane (150 mL) to provide the title compound (866 mg). $^1$H NMR (DMSO-d$_6$): 10.35 (s br, 1H), 10.02 (s br, 1H), 9.28 (s br, 1H), 6.94 (d, 2H, J=8.4 Hz), 6.65 (d, 2H, J=8.7 Hz), 6.27 (dd, 2H, J=10.2 Hz, 2.1 Hz), 3.92 (s, 2H); MS: 279 (MH$^+$).

3) Synthesis of 5-chloro-7-hydroxy-3-(4-hydroxyphenyl)-4-oxo-4H-1-benzopyran.

A solution consisting of 1-(2-chloro-4,6-dihydroxyphenyl)-2-(4-hydroxyphenyl)-ethanone (50 mg), acetic anhydride (1.2 mL) and sodium acetate (44 mg) was prepared. The solution was heated at 140° C. for 50 min, cooled to room temperature and stirred for 70 h. The soution was quenched with saturated sodium bicarbonate (10 mL), water (1 mL) and methanol (10 mL). After stirring for 3 h the solution was acidified to pH 5 with saturated potassium diphosphate and extracted with ethyl acetate (3×15 mL). The organics were dried over Na$_2$SO$_4$, filtered and concentrated in vacuo. The resulting yellow oil was diluted with toluene and dehydrated for 1.5 h using a Dean-Starke trap. Chromatography using reverse phase preperative HPLC provided the title compound (18 mg). $^1$H NMR (DMSO-$d_6$): 11.07 (s br, 1H), 9.46 (s br, 1H), 7.03 (d, 1H, J=8.4 Hz), 6.88 (d, 1H, J=2.4 Hz), 6.79 (s, 1H), 6.78 (d, 2H, J=8.7 Hz), 2.18 (s, 3H); MS: 303 (MH$^+$).

Synthetic Scheme for Example 11:

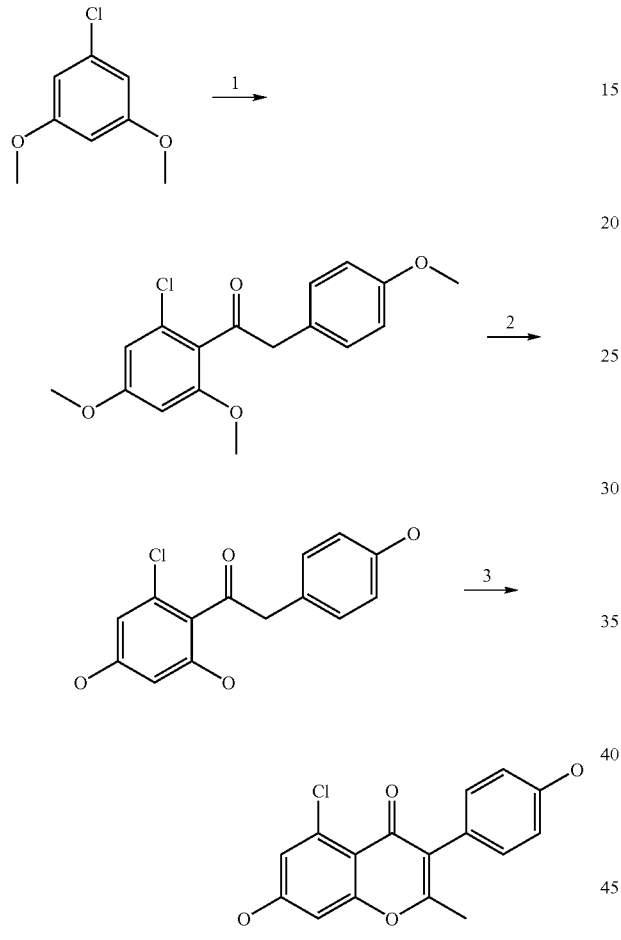

a therapeutically-effective amount of a ligand that satisfies the equation:

$$K_{i\alpha A}/K_{i\beta A} > 25,$$

wherein $K_{i\alpha A}$ is the $K_i$ value for the ligand in ER-α

$K_{i\beta A}$ is the $K_i$ value for the ligand in ER-β;

the ligand also having the structure

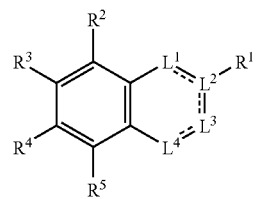

or a pharmaceutically acceptable salt thereof, wherein $L^1$ is =C(R$^6$)—, —CH(R$^6$)—;

$L^2$ is =C— or —CH—;

$L^3$ is —C(=O)—;

$L^4$ is O;

wherein when $L^1$ is —CH(R$^6$)—, $L^2$ 15 —CH—;

R$^a$ is independently at each occurrence H or (C$_1$–C$_5$)alkyl;

R$^1$ is phenyl;

R$^2$ is —SR$^a$, —NR$^a$R$^a$, —NC(=O)R$^a$, —NS(=O)R$^a$, —NS(=O)$_2$R$^a$, halogen, cyano, haloC$_{1-6}$alkyl, —CO$_2$R$^a$, —C(=O)R$^a$, —C(=O)NHR$^a$, nitro, —S(=O)R$^a$ or —S(=O)$_2$R$^a$;

R$^3$, R$^4$ and R$^5$ are independently selected from —R$^a$, —OR$^a$, —SR$^a$, —NR$^a$R$^a$, —NC(=O)R$^a$, —NS(=O)R$^a$, —NS(=O)$_2$R$^a$, halogen, cyano, haloC$_{1-6}$alkyl, —CO$_2$R$_a$, —C(=O)R$^a$, —C(=O)NHR$^a$, nitro, —S(=O)R$^a$ or —S(=O)$_2$R$^2$; and

| Example | Structure | FP ER-β $K_i$ (nM) (LOQ = 0.01 nM, upper limit 1000 nM) | FP ER-α $K_i$ (nM) (LOQ = 0.01 nM, upper limit 1000 nM) | FP Sel. Ratio |
|---|---|---|---|---|
| 11 | 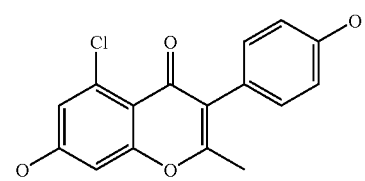 | 46.10 | 1000.00 | 32.8 |

The invention claimed is:

1. A pharmaceutical composition comprising:

R$^6$ is H, C$_{1-5}$ alkyl, phenyl or haloC$_{1-6}$alkyl.

* * * * *

UNITED STATES PATENT AND TRADEMARK OFFICE
CERTIFICATE OF CORRECTION

PATENT NO.        : 7,226,945 B2
APPLICATION NO.   : 10/399010
DATED             : June 5, 2007
INVENTOR(S)       : Barlaam et al.

Page 1 of 1

It is certified that error appears in the above-identified patent and that said Letters Patent is hereby corrected as shown below:

<u>Col. 20, line 25:</u> "$L_1$ is $=C(R^6)$-, $-CH(R^6)$-" should read -- $L_1$ is $=C(R^6)$- or $-CH(R^6)$- --.

<u>Col. 20, line 31:</u> "$L_2$ 15 -CH-" should read -- $L_2$ is -CH- --.

<u>Col. 20, line 35:</u> Between the word "is" and the word "phenyl" insert the word --substituted--.

<u>Col. 20, line 45:</u> "$-CO_2R_a$" should read -- $-CO_2R^a$ --.

<u>Col. 20, line 46:</u> "or" should read --and--.

<u>Col. 20, line 47:</u> "$-S(=O)_2R^2$" should read -- $-S(=O)_2R^a$ --.

Signed and Sealed this

Twenty-fourth Day of March, 2009

JOHN DOLL
*Acting Director of the United States Patent and Trademark Office*